United States Patent [19]

Claeson et al.

[11] 4,276,375

[45] Jun. 30, 1981

[54] DETERMINATION OF SERINE PROTEASES

[75] Inventors: Karl G. Claeson; Leif E. Aurell, both of Saro; Leif R. Simonsson, Hisings-Backa, all of Sweden

[73] Assignee: AB Kabi, Stockholm, Sweden

[21] Appl. No.: 86,970

[22] Filed: Oct. 22, 1979

Related U.S. Application Data

[62] Division of Ser. No. 852,006, Nov. 16, 1977, Pat. No. 4,207,232.

[30] Foreign Application Priority Data

Dec. 12, 1976 [SE] Sweden ................................ 7613463

[51] Int. Cl.$^3$ ........................... C12Q 1/56; C12Q 1/38
[52] U.S. Cl. ................................ 435/13; 260/112.5 R; 435/23
[58] Field of Search ................................... 435/23, 13; 260/112.5 R

[56] References Cited

U.S. PATENT DOCUMENTS

| | | | |
|---|---|---|---|
| 4,016,042 | 4/1977 | Svendsen .............................. 435/23 |
| 4,028,318 | 6/1977 | Anrell et al. ...................... 435/23 X |
| 4,061,625 | 12/1977 | Akenstam et al. ................. 435/13 X |
| 4,070,245 | 1/1978 | Svendsen .............................. 435/13 |
| 4,137,225 | 1/1979 | Ekenstam et al. ................. 435/23 X |

Primary Examiner—David M. Naff
Attorney, Agent, or Firm—Pollock, Vande Sande & Priddy

[57] ABSTRACT

Serine proteases in a substance such as blood are determined by contacting the substance with a novel chromogenic or fluorgenic substrate for serine proteinases and spectrophotometrically measuring the quantity of a chromophore or fluorescent compound released from the substrate by serine proteases in the substance. The novel substrate has the amino acid sequence-ILe-A-Gly-Arg-wherein A is Asp or Glu substituted in the carboxylic group by esterification or amidation. The novel substrate increases sensitivity and accuracy of the determination.

15 Claims, No Drawings

DETERMINATION OF SERINE PROTEASES

This is a division of application Ser. No. 852,006, filed Nov. 16, 1977, now U.S. Pat. No. 4,207,232.

This invention relates to new chromogenic substrates for serine proteases. The new substrates are suitable for the determination of factor Xa (E.C. 3, 4, 21.6) or for the study of reactions which cause Xa to be formed, inhibited or consumed or even for the determination of such factors that influence or participate in such reactions.

Factor X is a key substance in the series of reactions leading to the coagulation of blood. The activation of factor X brings about the formation of the proteolytic enzyme, factor Xa, which is directly responsible for the transference of prothrombin to thrombin. The transformation of prothrombin to thrombin by factor Xa involves the cleavage of two peptide bonds in the prothrombin molecule. These two cleavage sites are preceded by exactly the same amino acid sequence: -Ile-Glu-Gly-Arg-.

A simple method for the determination or coagulation factor Xa is very valuable for diagnostic purposes. The hitherto very best reagents for the determination of factor Xa consist of chromogenic peptide substrates with an amino acid sequence, -Ile-Glu-Gly-Arg-, corresponding to the sequence preceding the cleavage sites of the natural substrate prothrombin.

The substrate Benzoyl-Ile-Glu-Gly-Arg-p-nitroanilide (S-2222), which is the best substrate in this series, has an amino acid sequence identical to the above discussed part of the natural substrate. This substrate has already found application in clinical assays of e.g. antifactor Xa and Heparin (A. N. Teien, M Lie and U Abildgaard, Thrombosis Research 8, 413, 1976). The methods are based on the following reaction:

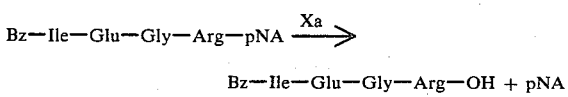

The released p-nitroanilide (pNA) has a light absorption maximum different from that of the substrate, and the enzymatic reaction can easily be followed by measuring the increase in absorption at 405 nm, which is proportional to the amount of active factor Xa.

A large number of synthetic substrates for factor Xa has been described by L Aurell, G Claeson, G Karlsson and P Friberger in Peptides 1976, p 191, Proc. from the XIVth European Peptide Symposium, Weipon, Belgium, 1976. The amino acids in the natural sequence were varied. They were in turn replaced by other similar amino acids, but in no case a better substrate than S-2222 was obtained. Even very small changes in the natural sequence, such as replacement of Ile by Leu, give substrates with much lower sensitivity.

The new chromogenic substrates, according to the invention, are represented by the following general formula:

$$R_1\text{-Ile-A-Gly-Arg-NH-}R_2$$

or salts thereof, wherein $R_1$ is acyl, preferably acetyl or benzoyl; $R_2$ is p-nitrophenyl, β-naphthyl or 4-methoxy-β-naphthyl, i.e. aromatic groups which give a chromophore or fluorescent compound, R-NH$_2$, at the enzymatic hydrolysis; A is Asp or Glu, substituted in the carboxylic group preferably by esterification or amidation. Suitable esters contain a short alkyl-, hydroxyalkyl-, substituted aminoalkyl- or cycloalkyl group. The esters employed contain 2–6 carbon atoms. Suitable amides contain mono- or disubstituted short alkyl-, hydroxyalkyl- or substituted aminoalkyl group, or a heterocyclic group in which the amido nitrogen forms part of a piperidine, morpheline or piperazine ring. The amides employed contain 1–6 carbon atoms.

The natural γ-carboxy group of Glu, which at biological pH has a negative charge and is hydrophilic, has according to the invention, been replaced by a considerably larger group, which is neutral and lipophilic. Since previous changes of the natural sequence. -Ile-Glu-Gly-Arg-, have only given inferior substrates (L Aurell, G Claeson, G Karlsson and P Friberger in Peptides 1976, p 191, Proc. from the XIVth European Peptide Symposium, Weipon, Belgium, 1976), it is very surprising that the comparatively big changes made in the invention have resulted in substrates with fundamentally better properties (see Table 1) than the previously best substrate, S-2222. The drastic lowering of the Michaelis constant (Km) is the most striking, and for pratical work, the most important improvement achieved with the new substrates. Km is defined as the substrate concentration required for the attainment of half of the maximal velocity (Vmax). The previous substrates and also the substrates according to the invention have limited solubilities, and for that reason the substrate concentration should be below 1 mM when working in buffer solution and blood plasma under practical conditions. With S-2222, which has Km=0.83 mM, one can only make full use of half of Vmax, whereas with the substrates in the invention, which have a 2 to 5 times lower Km, one can make much better use of the maximum velocity. Thus, obvious advantages are obtained when measuring factor Xa activity with the new substrates. Their sensitivity is several hundred percent higher than that of S-2222, which makes possible a much higher accuracy, a fundamentally lower sensitivity limit and a strongly decreased volume of the blood sample.

Assays of enzymes with the help of chromogenic substrates are very suitable for use in autoanalyzers, and the higher sensitivity of these new substrates brings about a shorter reaction time in the apparatus and with that also the possibility to analyze more samples per time-unit.

The new substrates according to the invention may be produced from chromogenic or fluorogenic substrates containing the amino acid sequences -Ile-Glu-Gly-Arg- and -Ile-Asp-Gly-Arg-, respectively, by esterification or amidation of the free γ- or β-carboxylic group with methods which are well known and commonly used in peptide chemistry.

The following examples illustrate the invention.

In the thin layer chromatographic analysis of eluates and products, glass plates with silica gel F$_{254}$ (Merck) were used as the absorption medium. The solvent system used is chloroform, methanol, acetic acid and water in the volume ratios 34:4:9:2.

After the thin layer chromatographing, the plates were studied first in UV-light (254 nm) and subsequently by using the chlorine/toluidine-reaction (G Pataki, Dünnschichtchromatografie in der Aminosäure- und Peptidchemie, Walter de Gruyter & Co Berlin, p 125, 1966) as a development method.

The meanings of the abbreviations used below are as follows:

Amino acids:

These abbreviations refer to amino acid rates. The free amino acid or peptide is indicated by means of H— at the amino group and —OH at the carboxyl group. The amino group is always indicated to the left, the carboxyl group to the right.

Unless otherwise stated, all amino acids used have the L-configuration.

Arg = Arginine
Asp = Aspartic acid
Glu = Glutamic acid
Gly = Glycine
Ile = Isoleucine
Leu = Leucine Further abbreviations:

Ac = Acetyl
AcOH = Acetic acid
Bz = Benzoyl
DCCI = Dicyclohexylcarbodiimide
DMF = Dimethylformamide
Et$_3$N = Triethylamine
HOBT = α-Hydroxybenzotriazol
HOSu = N-Hydroxysuccinimide
MeOH = Methanol
OEt = Ethyloxy
OMe = Methyloxy
OpNp = p-Nitrophenoxy
OisoPr = iso-Propyloxy
pNA = p-Nitroanilide
QAE = Quaternary amino-ethylsepharose (Pharmacia Fine Chemicals)
SOCl$_2$ = Thionylchloride

EXAMPLE 1

Bz-Ile-Glu(OMe)-Gly-Arg-pNA.HCl (M.w. 748.2)

Under moisturefree conditions, at 0° C., 30 μl of distilled SOCl$_2$ is added to 0.5 ml of absolute methanol. After the first lively reaction the solution is left for about 15 min at room temperature, and 75 mg (0.10 mmole) of Bz-Ile-Glu-Gly-Arg-pNA.HCl (S-2222) is added. The solution is stirred for 5 hours and then evaporated. The oil obtained is dissolved in a small amount of methanol and purified by gel chromatography on a column containing Sephadex LH-20 (Pharmacia Fine Chemicals) in methanol with methanol as eluating means. The pure methyl ester, obtained after evaporation of the methanol, is dissolved in water and lyophilized.

Yield: 30 mg (40%)
Homogenous according to TLC, R$_f$ = 0.33
$[\alpha]_D^{20}$ −40.3° (c 0.5, 50% HOAc/H$_2$O)

EXAMPLE 2

Bz-Ile-Glu(OEt)-Gly-Arg-pNA.HCl (M.w. 762.2)

Under moisturefree conditions, at −10° C., 60 μml or distilled SOCl$_2$ is added to 1.0 ml of absolute ethanol. After 30 min at room temperature 150 mg of S-2222 is added. When the reaction is finished after about 15 hours (according to TLC), the solution is evaporated. The oil obtained is dissolved in a small amount of 30% HOAc in H$_2$O and is purified by chromatography on a column containing Sephadex G 15 (Pharmacia Fine Chemicals) in 10% HOAc in H$_2$O. The pure ethyl ester from the eluate is lyophilized.

Yield: 70 mg (46%)
Homogenous according to TLC, R$_f$ = 0.40
$[\alpha]_D^{20}$ −37.7° (c 0.5, 50% HOAc/H$_2$O)

EXAMPLE 3

Bz-Ile-Glu(OisoPr)-Gly-Arg-pNA.HCl (M.w. 776.3)

The synthesis is performed according to the method of Example 2 but absolute isopropanol is used instead of ethanol. The reaction is completed after 16 hours. Chromatography and lyophilization is performed according to these procedures in Example 2.

Yield: 90 mg (58%)
Homogenous according to TLC, R$_f$ = 0.44
$[\alpha]_D^{20}$ −36.4° (c 0.5, 50% HOAc/H$_2$O)

EXAMPLE 4

Bz-Ile-Glu(O-cyclohexyl)-Gly-Arg-pNA.HCl (M.w. 833.3)

60 μl SOCl$_2$ is added to 1.0 ml of dry cyclohexanol, and after 1 hour at room temperature 200 mg S-2222 is added. When the reaction is finished after about 12 hours the solution is evaporated and chromatographed according to these procedures in Examples 2 and 3, whereupon the product is lyophilized.

Yield: 170 mg (75%)
Homogenous according to TLC, R$_f$ = 0.50
$[\alpha]_D^{20}$ −38.6° (c 0.5, 50% HOAc/H$_2$O)

EXAMPLE 5

Bz-Ile-Glu(O-CH$_2$CH$_2$N(CH$_3$)$_2$)-Gly-Arg-pNA.HCl (M.w. 859.8)

75 mg (0.10 mmole) of S-2222 and 100 mg (0.8 mmole) of dimethylaminoethanol hydrochloride are dissolved in 1.0 ml of dry distilled DMF, whereupon 10 μl of pyridin, 10 mg of HOBT (0.074 mmole) and finally 25 mg (0.12 mmole) of DCCI are added. The dicyclohexylurea formed is filtered after about 24 hours, and the DMF solution evaporated under reduced pressure. The remaining oil is dissolved in a small amount of 95% MeOH—5% H$_2$O and purified on a column containing QAE-25 ion exchanger in its chloride form. The same solvent mixture is used as eluant. By this procedure the hydrochloride of the dimethylaminoethyl ester is obtained free from other peptides, but contains some minor impurities, e.g. dimethylaminoethanol hydrochloride. The fraction containing the dimethylaminoethyl ester is evaporated and purified by chromatography on a column containing Sephadex G15 (Pharmacia Fine Chemicals) in 10% HOAc/H$_2$O. The solution of the pure ester is lyophilized. Yield: 60 mg (58%)

Homogenous according to TLC, R$_f$ = 0.50
$[\alpha]_D^{20}$ −35.0° (c 0.5, 50% HOAc/H$_2$O)

EXAMPLE 6

Bz—Ile—Glu—Gly—Arg—pNA · HCl (M.w. 775.3)
         |
         CONH—CH(CH$_3$)$_2$ 240 mg (0.33 mmole) of S-2222 and 45 mg (0.39 mmole) of HOSu are dissolved in 1 ml of dry distilled DMF. The solution is cooled to −5° C. and 120 mg (0.58 mmole) of DCCI is added. The temperature is allowed to rise to room temperature and after 4 hours the solution is again cooled down to 0° C. and the precipitated dicyclohexylurea is filtered and washed. The DMF solution (about 2 ml) is cooled to 0° C. and 0.1 ml of pure isopropylamine is added. After about 70 hours at room temperature the solution is evaporated under reduced pressure, mixed with 5 ml of water and again evaporated. The product is dissolved in about 4 ml of 50% HOAc/H₂O and is purified by chromatography on a column containing Sephadex G15 (Pharmacia Fine Chemicals) in 33% HOAc/H₂O. The same solvent mixture is used as eluant. The faction containing the pure isopropylamide is evaporated and is ion-exchanged on a column containing quaternary aminoethylsepharose, QAE25 (Pharmacia Fine Chemicals) in its chloride form in 95% MeOH 5% H₂O. The eluate is evaporated, dissolved in water and lyophilized.

Yield: 120 mg (47%)
Homogenous according to TLC, $R_f$=0.39.
$[\alpha]_D^{25}$ −30.6° (c 0.5, MeOH)

EXAMPLE 7

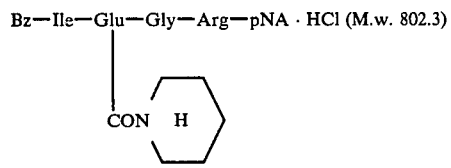

Bz—Ile—Glu—Gly—Arg—pNA · HCl (M.w. 802.3)

The synthesis is performed according to the method of Example 6 but piperidine is used instead of isopropylamine.

Yield: 105 mg (40%)
Homogenous according to TLC, $R_f$=0.50
$[\alpha]_D^{25}$ −34° (c 0.5, MeOH)

EXAMPLE 8

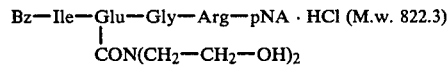

Bz—Ile—Glu—Gly—Arg—pNA · HCl (M.w. 822.3)
|
CON(CH₂—CH₂—OH)₂

The synthesis is performed according to the method of Example 6 but diethanolamine is used instead of isopropylamine.

Yield: 120 mg (45%)
Homogenous according to TLC, $R_f$=0.25
$[\alpha]_D^{25}$ −31° (c 0.5, MeOH)

EXAMPLE 9

Bz-Ile-Asp(OisoPr)-Gly-Arg-pNA.HCl (M.w. 762.3)

30 μl of distilled SOCl₂ is added to 0.5 ml of dry isopropanol, and after 30 min at room temperature 73 mg (0.10 mmole) of Bz-Ile-ASP-Gly-Arg-pNA.HCl (M.w. 720.2) is added. When the reaction is finished after about 18 hours the solution is evaporated, chromatographed and lyophilized according to these procedures in Examples 2, 3 and 4.

Yield: 32 mg (42%)
Homogenous according to TLC, $R_f$=0.46
$[\alpha]_D^{23}$ −22.7° (c 0.5, 50% HOAc/H₂O)

EXAMPLE 10

Bz-Ile-Asp(OEt)-Gly-Arg-pNA.HCl (M.w. 748.2)

The synthesis is performed according to the method of Example 9 but ethanol is used instead of isopropanol.
Yield: 28 mg (37%)
Homogenous according to TLC, $R_f$=0.40
$[\alpha]_D^{23}$ −23.5° (c 0.5, 50% HOAc/H₂O)

EXAMPLE 11

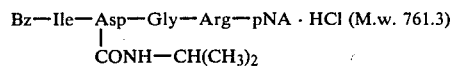

Bz—Ile—Asp—Gly—Arg—pNA · HCl (M.w. 761.3)
|
CONH—CH(CH₃)₂

The synthesis is performed according to the method of Example 6 but Bz-Ile-Asp-Gly-Arg-pNA.HCl is used as starting material instead of S-2222.

Yield: 100 mg (40%)
Homogenous according to TLC, $R_f$=0.40
$[\alpha]_D^{25}$ −20.1° (c 0.5, MeOH)

EXAMPLE 12

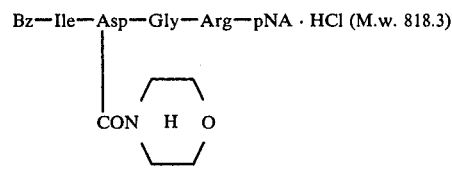

Bz—Ile—Asp—Gly—Arg—pNA · HCl (M.w. 818.3)

The synthesis is performed according to the method of Example 11, but morpholine is used instead of isopropylamine.

Yield: 95 mg (35%)
Homogenous according to TLC, $R_f$=0.46
$[\alpha]_D^{25}$ −24.2° (c 0.5, MeOH)

Determination of Km and Vmax

Km and Vmax are obtained by means of the Lineweaver-Burk equation:

$$\frac{1}{v_o} = \frac{Km}{V\max} \cdot \frac{1}{S_o} + \frac{1}{V\max}$$

Enzyme and substrate are mixed in a buffer solution and the rate of hydrolysis is measured spectrophotometrically. The substrate concentration ($S_o$) is varied while the enyzme concentration is kept constant. The reciprocal velocity $1/v_o$ is then plotted against the reciprocal substrate concentration $1/S_o$, and Km and Vmax are estimated (Table 1) from the obtained Lineweaver-Burk diagram.

| Reagents | | |
|---|---|---|
| Buffer | Tris (tris(hydroxymethyl)aminomethane) 0.05 mole/l, pH = 8.3, I = 0.25 (NaCl) | |
| Enzyme | Diagen (6.4 Denson U) (Diagnostic Reagents) . 1 ampule is dissolved in 2 ml of water. | |
| Substrate | The substrate is dissolved in water to 2 mmole/l. | |
| Method | Buffer, +37° C. 2400–1850 μl | |
| | Enzyme, +20° C. 50 μl } 2500 μl | |
| | Substrate, +37° C. 50–600 μl | |
| | Mix and read change of absorbance (Δ OD/min) at 405 nm and at 37° C. | |
| Relative activity | Buffer, +37° C. 2200 μl | |
| | Enzyme, +20° C. 50 μl | |
| | Substrate, +37° C. 250 μl | |
| | Mix and read change of absorbance (Δ OD/min) at 405 nm and at 37° C. | |

TABLE 1

| | Km, Vmax and Relative activities | | |
|---|---|---|---|
| Substrate | Km · 10⁴ mol/l | Vmax · 10⁸ mol/min · U | Relative activity |
| S-2222 | 8.3 | 8.6 | 100 |

TABLE 1-continued

| | Km, Vmax and Relative activities | | |
|---|---|---|---|
| Substrate | $Km \cdot 10^4$ mol/l | $Vmax \cdot 10^8$ mol/min $\cdot$ U | Relative activity |
| Ex. 1 | 2.6 | 8.1 | 230 |
| Ex. 2 | 2.9 | 7.5 | 200 |
| Ex. 3 | 2.1 | 7.1 | 220 |
| Ex. 6 | 5.6 | 20.0 | 340 |
| Ex. 7 | 1.7 | 8.6 | 300 |

What we claim is:

1. A method for diagnostic determination of serine proteases which comprises contacting a substance in which said determination of serine poteases is desired with a chromogenic or fluorogenic enzyme substrate containing the sequence -Ile-A-Gly-Arg-$R_2$ where A is Asp or Glu, substituted in the carboxylic group by esterification or amidation, wherein the esters contain a short chain alkyl or hydroxyalkyl or alkyl-substituted aminoalkyl or cycloalkyl group containing a total of 2-6 carbon atoms, and the amides contain mono or di-substituted short chain alkyl or hydroxyalkyl or alkyl-substituted aminoalkyl group containing a total of 1-6 carbon atoms or a heterocyclic group in which the amido nitrogen forms part of a piperidine, a morpholine or a piperazine ring, and $R_2$ is a group which gives a chromophore or fluorescent compound upon enzymatic hydrolysis, and then spectrophotometrically measuring the quantity of chromophore or fluorescent compound released from said substrate by enzymatic hydrolysis of the substrate by serine proteases in said substance.

2. The method of claim 1 wherein said serine proteases is factor Xa.

3. The method of claim 1 wherein said substrate has the formula $R_1$-Ile-A-Gly-Arg-NH-$R_2$ wherein $R_1$ is acyl.

4. The method of claim 3 wherein $R_1$ is acetyl.

5. The method of claim 3 wherein $R_1$ is benzoyl.

6. The method of claim 3 wherein $R_2$ is p-nitrophenyl or β-naphthyl or 4 methoxy-β-naphthyl or salt thereof.

7. The method of claim 1 wherein A is Asp or Glu substituted with a methoxy group.

8. The method of claim 1 wherein A is Asp or Glu substituted with an ethoxy group.

9. The method of claim 1 wherein A is Asp or Glu substituted with an isopropoxy group.

10. The method of claim 1 wherein A is Asp or Glu substituted with a cyclohexoxy group.

11. The method of claim 1 wherein A is Asp or Glu substituted with a dimethylaminoethoxy group.

12. The method of claim 1 wherein A is Asp or Glu substituted with $CONHCH(CH_3)_2$.

13. The method of claim 1 wherein A is Asp or Glu substituted with

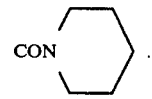

14. The method of claim 1 wherein A is Asp or Glu substituted with $CON(CH_2CH_2OH)_2$.

15. The method of any of claims 7-14 wherein said substrate has the formula $R_1$-Ile-A-Gly-Arg-NH-$R_2$ wherein $R_1$ is benzoyl and $R_2$ is p-nitrophenyl.

* * * * *